(12) United States Patent
McDole et al.

(10) Patent No.: US 11,373,400 B1
(45) Date of Patent: Jun. 28, 2022

(54) METHODS AND SYSTEMS FOR IMAGE PROCESSING TO PRESENT DATA IN AUGMENTED REALITY

(71) Applicant: Express Scripts Strategic Development, Inc., St. Louis, MO (US)

(72) Inventors: Matt D. McDole, St. Charles, MO (US); Sivaram Adhiappan, St. Charles, MO (US); Robert K. Gaddy, St. Louis, MO (US); Carlos G. Ruiz, St. Louis, MO (US); Murat Sanli, Kirkwood, MO (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 1 day.

(21) Appl. No.: 16/356,458

(22) Filed: Mar. 18, 2019

(51) Int. Cl.
  *G06V 20/20* (2022.01)
  *G06T 19/00* (2011.01)
  *G16H 80/00* (2018.01)
  *G06K 7/14* (2006.01)

(52) U.S. Cl.
  CPC ............ *G06V 20/20* (2022.01); *G06K 7/143* (2013.01); *G06K 7/1443* (2013.01); *G06T 19/006* (2013.01); *G16H 80/00* (2018.01)

(58) Field of Classification Search
  CPC .. G06K 9/00671; G06K 7/143; G06K 7/1443; G06T 19/006; G16H 80/00
  See application file for complete search history.

(56) References Cited

U.S. PATENT DOCUMENTS

| | | | |
|---|---|---|---|
| 9,852,261 B1* | 12/2017 | Havard | G06Q 50/22 |
| 10,529,028 B1* | 1/2020 | Davis | G06Q 40/08 |
| 2014/0168478 A1* | 6/2014 | Baheti | G06K 9/3258 |
| | | | 348/240.99 |
| 2014/0257843 A1* | 9/2014 | Adler | G09F 3/10 |
| | | | 283/81 |
| 2014/0267647 A1* | 9/2014 | Wexler | G06V 30/418 |
| | | | 348/62 |

(Continued)

FOREIGN PATENT DOCUMENTS

| | | |
|---|---|---|
| EP | 3306443 A1 | 4/2018 |
| EP | 3312801 A1 | 4/2018 |

(Continued)

*Primary Examiner* — Sing-Wai Wu
*Assistant Examiner* — Khoa Vu
(74) *Attorney, Agent, or Firm* — Husch Blackwell LLP

(57) ABSTRACT

Methods and systems for displaying information in augmented reality are described. In one embodiment, a system comprises a camera, a memory, a display, and a processor configured to (a) detect a first prescription drug in a field of view of a camera by detecting a glyph printed on a label on a container of the first prescription drug, (b) determine a first identifier associated with the first prescription drug using optical character recognition, (c) determine whether a user has access to additional data about the first prescription drug, (d) request the additional data about the first prescription drug from a database, and (e) display the additional data in augmented reality adjacent to the first prescription drug on the display such that the additional data moves when the field of view of the camera changes such that the additional data remains displayed adjacent to the first prescription drug.

17 Claims, 8 Drawing Sheets

(56) References Cited

U.S. PATENT DOCUMENTS

| | | | |
|---|---|---|---|
| 2016/0028917 A1* | 1/2016 | Wexler | G02B 27/0093 348/169 |
| 2016/0314276 A1* | 10/2016 | Wilz, Sr. | G06F 19/3462 |
| 2017/0323062 A1* | 11/2017 | Djajadiningrat | G06F 19/324 |
| 2017/0351094 A1 | 12/2017 | Poulos et al. | |
| 2017/0352184 A1 | 12/2017 | Poulos et al. | |
| 2017/0358135 A1 | 12/2017 | Trehan | |
| 2017/0358140 A1 | 12/2017 | Kohler et al. | |
| 2018/0080774 A1 | 3/2018 | Sink et al. | |
| 2018/0225818 A1* | 8/2018 | Jacobs | G06K 9/00 |
| 2020/0082561 A1* | 3/2020 | Karonchyk | G01C 21/30 |
| 2021/0042724 A1* | 2/2021 | Rathod | G06Q 30/06 |

FOREIGN PATENT DOCUMENTS

| | | | |
|---|---|---|---|
| EP | 3318945 | A2 | 5/2018 |
| WO | 2017208148 | A1 | 12/2017 |
| WO | 2017208494 | A1 | 12/2017 |
| WO | 2018004232 | A1 | 1/2018 |
| WO | 2018005878 | A1 | 1/2018 |
| WO | 2018032083 | A1 | 2/2018 |
| WO | 2018039270 | A1 | 3/2018 |

\* cited by examiner

METHODS AND SYSTEMS FOR IMAGE PROCESSING TO PRESENT DATA IN AUGMENTED REALITY

FIELD

The present disclosure relates generally to the technical field of augmented reality. In a specific example, the present disclosure may relate to using augmented reality with prescription drugs.

BACKGROUND

Conventional prescription drug bottles generally include a label displaying a limited amount of printed information. The conventional prescription pill bottles generally display patient name, drug name, and limited instructions for using or taking the prescription drug. However, the information printed on the label is hard to read, can be lost (e.g. by scratching off information or the label accidentally being removed), and can include errors or typos. As such, there is a continuing need to improve how drug information associated with a prescription drug is communicated to a patient.

DETAILED DESCRIPTION

Figure 1:
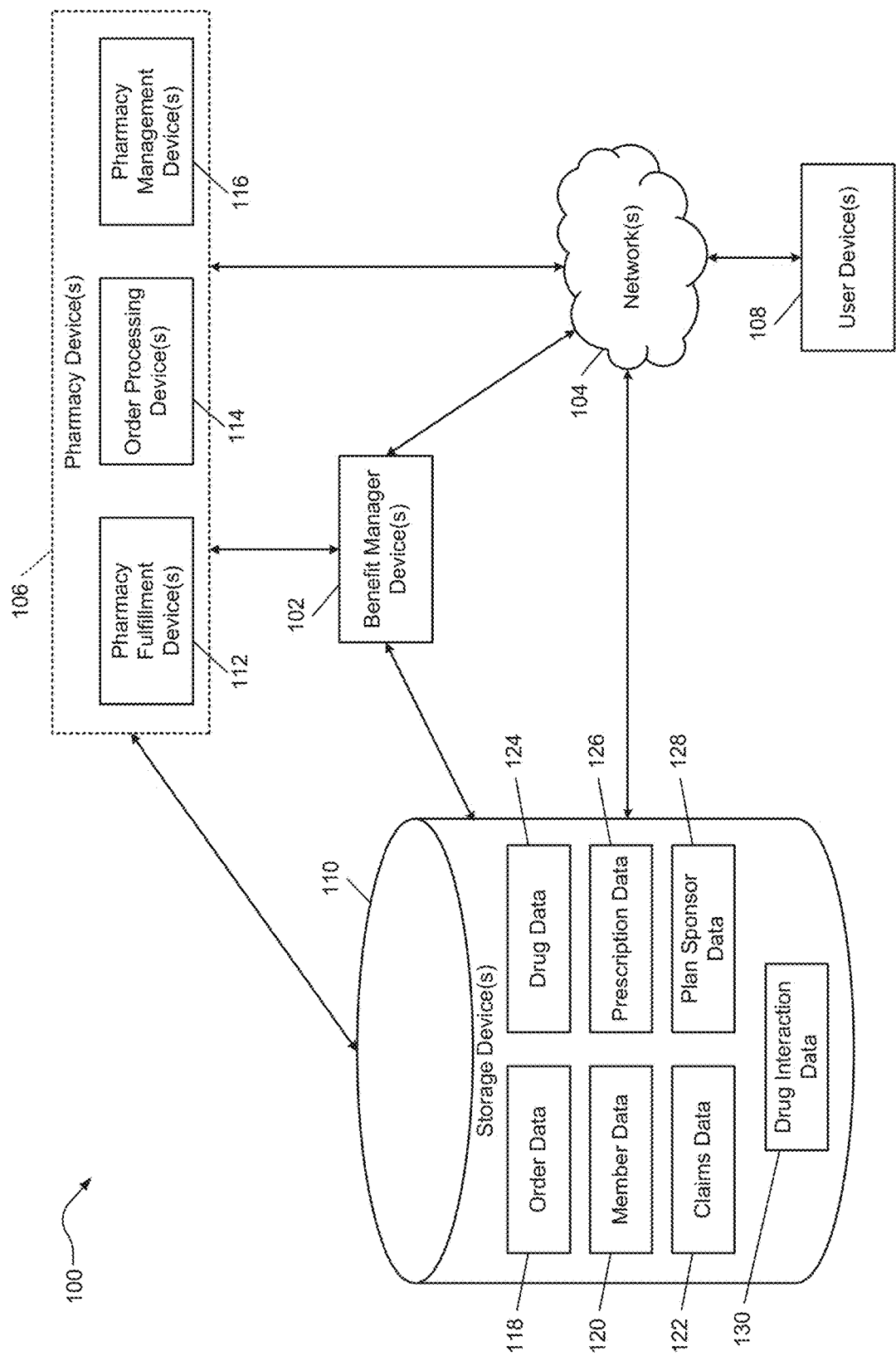
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device 108, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The user device 108 may be a stand-alone device that solely provides at least some of the functionality to enable augmented reality, or may be a multi-use device that has functionality outside of augmented reality functions as described herein. Examples of the user device 108 include a set-top box (STB), a receiver card, a mobile telephone, a personal digital assistant (PDA), a display device, a portable gaming unit, and a computing system; however, other devices may also be used. For example, the user device 108 may include a mobile electronic device, such an IPHONE or IPAD device by Apple, Inc., mobile electronic devices powered by ANDROID by Google, Inc., and a BLACKBERRY device by Research In Motion Limited. The user device 108 also include other computing devices, such as desktop computing devices, notebook computing devices, netbook computing devices, gaming devices, and the like. Other types of electronic devices may also be used. Furthermore, the user device 108 can include a camera or can interface with a camera for the visual detection of glyphs or a prescription pill bottle. Also, the user device 108 can include a display (e.g. a touch screen) that can display additional information about a prescription drug in augmented reality. Additionally or alternatively, the user device 108 can execute an application that may use a cellular phone function of the user device 108. The application may include instructions that when executed on the user device 108, in the benefit manager device 102, or pharmacy device 106, cause a machine to change its state or perform tasks within the machine and with other machines.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/ or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc. In addition, the member data 112 can include or reference prescription numbers associated with the member.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

Furthermore, the claims data 122 can include or reference past prescriptions associated with previous refills, if any, of a prescription drug, how many pills or doses of the prescription drug are in each refill for the member, a last refill date (i.e. when the prescription drug was last refilled), a doctor who prescribed the prescription drug, and contact information for the doctor who prescribed the prescription drug. In some embodiments, the claims data 122 can predict how many pills or doses remain in the prescription based on a current date, the last refill date, and prescription dosing instructions. For example, if the prescription fill included 30 pills to be taken daily, the prescription was filled on Jan. 1, 2018, and the current date is Jan. 15, 2018, the claims data 122 can predict that 15 pills remain. In some embodiments, the claims data 122 and the number of pills or doses remaining are updated upon receiving indication that the member took or used the prescription drug. For example, a reminder application can receive an indication that the drug was used by the member over the network 104.

The drug data 124 may include drug name (e.g., technical name and/or common name), other names by which the drug is known, active ingredients, an image of the drug (such as in pill form), typical dosing instructions, etc. The drug data 124 may include information associated with a single medication or multiple medications. However, dosing instructions may come from the claims data 122 if the doctor prescribed dosing instructions different from the typical dosing instructions.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

Furthermore, the drug interaction data 130 can include all known interactions between various prescription drugs. The known interactions can be negative, positive, or benign. Further still, the drug interaction data 130 can include known interactions between each prescription drug and over-the-counter drugs, known interactions between each prescription drug and vitamins or medical herbs (e.g. St. John's Wort), or known interactions between each prescription drug and commonly used substances, such as alcohol.

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
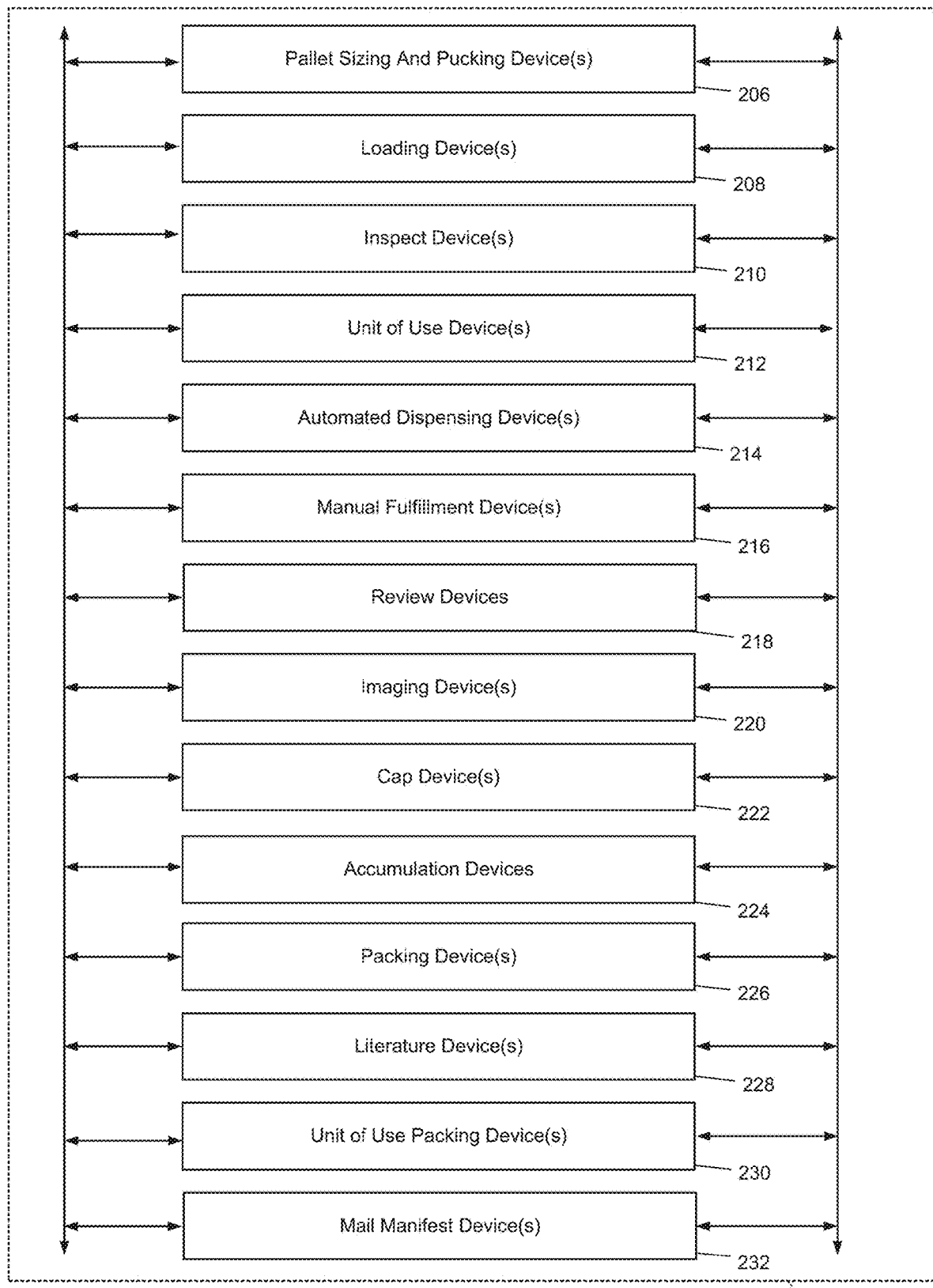
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
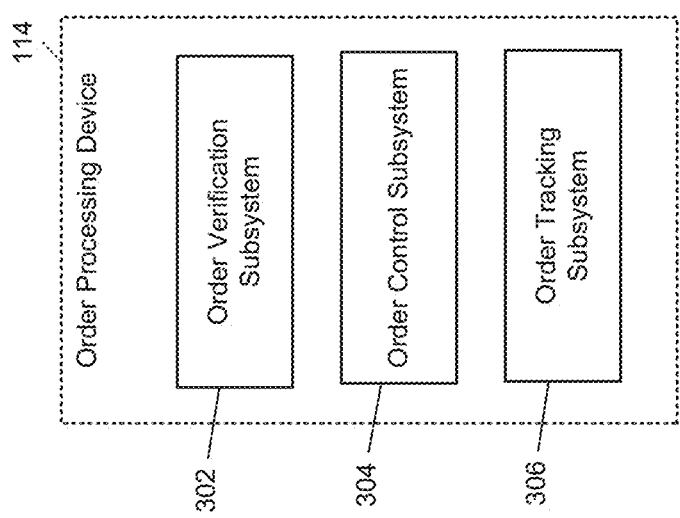
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Example methods and systems for using augmented reality are described. In the following description, for purposes of explanation, numerous specific details are set forth in order to provide a thorough understanding of example embodiments. It will be evident, however, to one of ordinary skill in the art that embodiments of the present disclosure may be practiced without these specific details.

After the benefit manager device 102 adjudicates and dispenses a prescription drug to a member, the benefit manager device 102 can respond to data inquiries from the user device 108 and provide additional information, for presentation in augmented reality, to the user device 108. After receiving the additional information, the user device 108 can display the additional information to the member in augmented reality. The additional information can include a member name, a prescription number, a photograph of an individual pill of the prescription drug, a name of the prescription drug, a quantity of the prescription drug, a number of refills, a last fill date, a prescription expiration date, a prescribing doctor, and a prescribing doctor's phone number. In addition, the user device 108 can display activation buttons in augmented reality that, when activated, function to call the prescribing doctor or refill the prescription.

Figure 4:
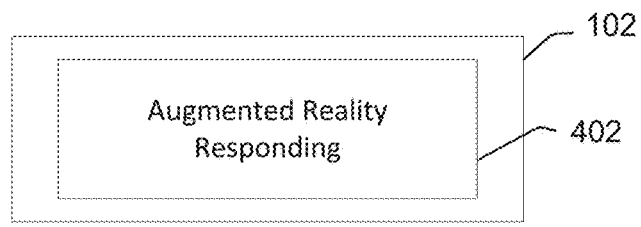
FIG. 4 is a block diagram of an example benefit manager device that may be deployed within the system of FIG. 1, according to an example embodiment.

FIG. 4 illustrates the benefit manager device 102, according to an example embodiment. The benefit manager device 102 may be deployed in the system 100, or may otherwise be used.

The benefit manager device 102 may include an augmented reality data providing subsystem 402. In some embodiments, the augmented reality data providing subsystem 402 may provide server-side functionality to the user device 108. By way of example, the augmented reality data providing subsystem 402 may be deployed in both the user device 108 and the benefit manager device 102. The user device 108 may then perform some of the functionality while other functionality is performed by the benefit manager device 102. The augmented reality data providing subsystem 402 may receive requests from the user device 108 and provide data to the user device 108 in response to the requests. Such provided data can include additional data about a pharmaceutical drug to be displayed in augmented reality or drug interaction data to be displayed in augmented reality.

Figure 5:
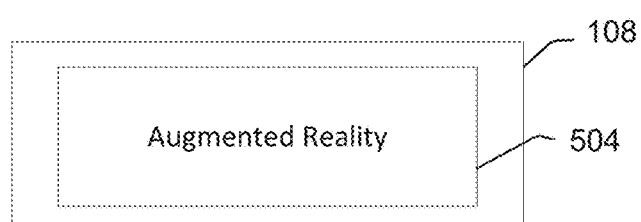
FIG. 5 is a block diagram of an example user device that may be deployed within the system of FIG. 1, according to an example embodiment.

FIG. 5 illustrates the user device 108, according to an example embodiment. The user device 108 may include an augmented reality subsystem 504. In some embodiments, the augmented reality subsystem 504 may provide client-side functionality and interact with the augmented reality data providing subsystem 402. The augmented reality subsystem 504 may comprise or be part of an application installed on the user device 108. The augmented reality subsystem 504 can detect pharmaceutical drugs in a camera's field of view, recognize printed information associated with the pharmaceutical drug, and display additional information, received from the augmented reality data providing subsystem 402, about the pharmaceutical drug in augmented reality.

Figure 6:
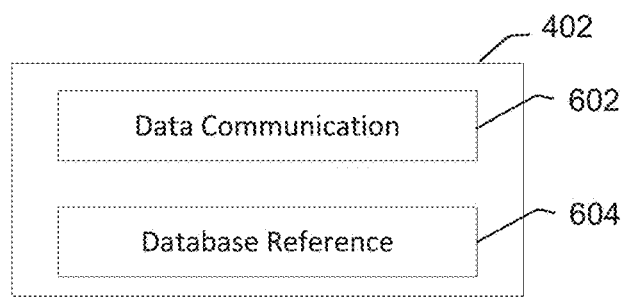
FIG. 6 is a block diagram of an example augmented reality data providing subsystem that may be deployed within the benefit manager device of FIG. 4, according to an example embodiment.

FIG. 6 illustrates an example augmented reality data providing subsystem 402 that may be deployed in the benefit manager device 102 or otherwise deployed in another system. One or more modules are communicatively coupled and included in the augmented reality data providing subsystem 402 to enable the benefit manager device 102 to provide additional information about a prescription drug to the user device 108. The modules of the augmented reality data providing subsystem 402 that may be included are a data communication module 602 and a database reference module 604. Other modules may also be included.

In some embodiments, the modules of the augmented reality data providing subsystem 402 may be distributed so that some of the modules are deployed in the user device 108, some modules are deployed in the benefit manager device 102, and some module are deployed in the pharmacy device 106. In one embodiment, the modules are deployed in memory and executed by a processor coupled to the memory. The functionality contained within the modules 602-604 may be combined into a lesser number of modules, further divided among a greater number of modules, or redistributed among existing modules. Other configurations including the functionality of the modules 602-604 may be used.

The data communications module 602 can receive data requests from the user device 108 for information to display in augmented reality and can transmit the information to be displayed in augmented reality based on the request. For example, the data communication module 602 can receive a prescription number from the user device 108, and the data communication module 602 can pass the prescription number to the database reference module 604. The database reference module 604 can gather data related to the prescription number in the database 110, such as prescription drug name, prescription drug nickname, a photograph of a pill of the prescription drug, a number of pills or doses remaining of the prescription drug, a prescribing doctor, or any other information related to the prescription number. The database reference module 604 can provide the gathered data to the communication module 602, and the communication module 602 can transmit the data related to the prescription number to the user device 108. If more than one prescription number are provided, or the data communication module 602 also receives indication of another substance (e.g. an over-the-counter drug, a medical herb, or a vitamin) with the prescription number, the database reference module 604 may gather the drug interaction data 130 related to the prescription drug and the another substance or multiple prescription drugs.

Figure 7:
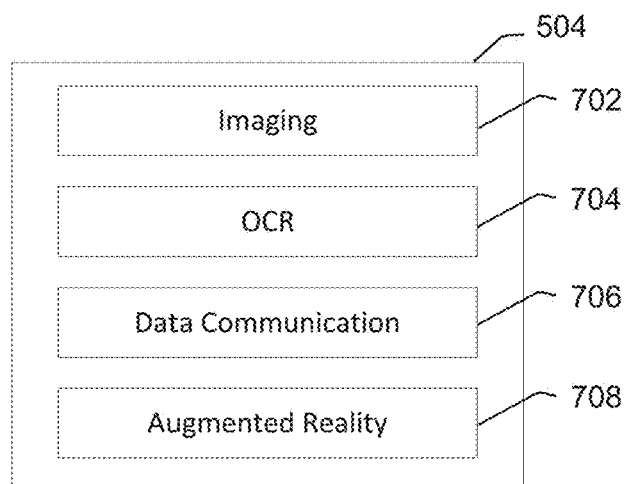
FIG. 7 is a block diagram of an example augmented reality subsystem that may be deployed within the user device of FIG. 5, according to an example embodiment.

FIG. 7 illustrates an example augmented reality subsystem 504 that may be deployed in the user device 108 or otherwise deployed in another system. One or more modules are communicatively coupled and included in the augmented reality subsystem 504 to enable the user device 108 to display additional information about a prescription drug in augmented reality. The modules of the augmented reality subsystem 504 that may be included are an imaging module 702, an optical character recognition (OCR) module 704, a user device data communication module 706, and an augmented reality module 708. Other modules may also be included.

The imaging module 702 can receive images from a camera that captures the images of a field of view. The imaging module 702 can analyze the images to determine whether the images include a prescription pill bottle or other prescription drug container. In an exemplary embodiment, the imaging module 702 can search a captured image for a unique glyph to be included on a label of the prescription pill bottle or other prescription drug container. Alternatively, the imaging module 702 can compare one or more 3D image models of a prescription pill bottle or other prescription containers to objects in a captured image to determine whether the prescription pill bottle or other prescription drug container is within the camera's field of view.

When the imaging module 702 detects a prescription pill bottle or other prescription drug container, the imaging module 702 can trigger the OCR module 704. The OCR module 704 can receive the image determined to have the prescription pill bottle or other prescription drug container and search for a prescription number or other unique identifier printed on the label. In some embodiments, the prescription number can be printed directly below the glyph. In some embodiments, the OCR module 704 can de-warp or unwarp the image when the unique identifier is printed on a rounded surface, like a prescription pill bottle. The OCR module 704 can detect and determine the prescription number associated with the prescription pill bottle or other prescription drug container using optical character recognition.

The user device data communications module 706 can transmit a data requests for information to display in augmented reality and can receive the information to be displayed in augmented reality from the benefit manager device 102. For example, the user device data communication module 706 can transmit the prescription number and can receive additional data associated with a prescription drug from the benefit manager device 102. The user device data communication module 706 can pass the received data from the benefit manager device 102 to the augmented reality module 708.

The augmented reality module 708 can display the information received from the benefit manager device 102 on a display screen of the user device 108 in augmented reality. In other words, the augmented reality module 708 can display real-time images captured from the camera of the user device 108 and also display additional information adjacent to a detected prescription pill bottle or other prescription drug container superimposed over the real-time images. Regardless of where the prescription pill bottle or other prescription drug container is on the display screen, the additional information can always be displayed adjacent to the prescription pill bottle or other prescription drug container. As such, if the field of view of the camera moves, the additional information can move as well to remain displayed adjacent to the prescription pill bottle or other prescription drug container. The additional information can be displayed to the right of the prescription pill bottle or other prescription drug container, the left of the prescription pill bottle or other prescription drug container, above the prescription pill bottle or other prescription drug container, below the prescription pill bottle or other prescription drug container, or whether the most screen space exists.

Additionally, the augmented reality module 708 can present interactive buttons on the display screen, which can be a touch screen. In response to a user activating (e.g. touching) a portion of the display screen associated with the current position of one of the interactive buttons, the augmented reality module 708 can perform an action. For example, one of the interactive buttons can result in the user device 108 transmitting a request to refill the prescription drug over the network 104, and one of the interactive buttons can call a doctor who prescribed the prescription drug using a cell phone function of the user device 108. Because the buttons can move in augmented reality with movement of the field of view of the camera, the portion of the display screen associated with the current positon of the interactive buttons can change with the movement of the field of view of the camera.

Figure 8:
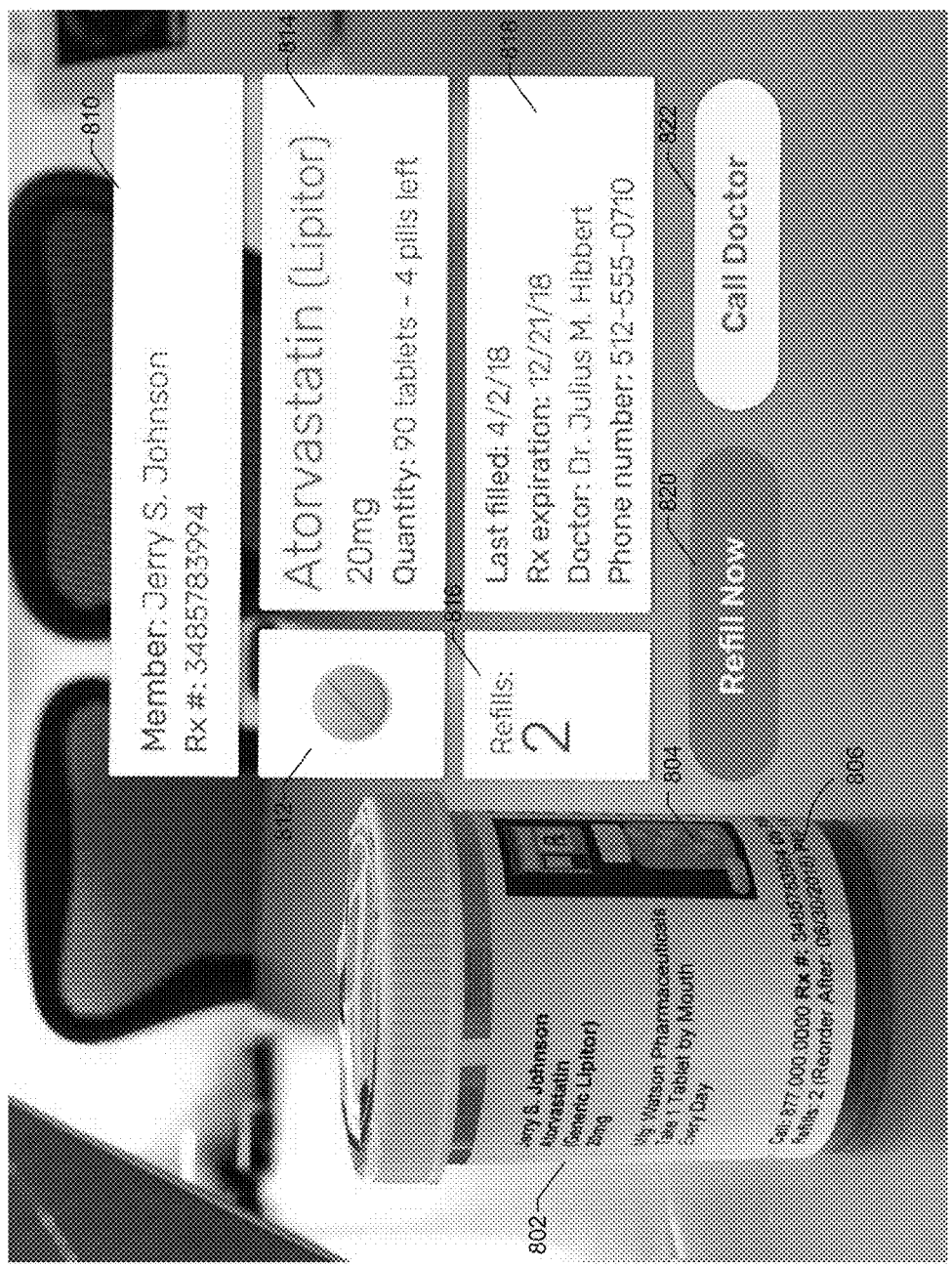
FIG. 8 is a screenshot illustrating additional data about a pharmaceutical drug displayed in augmented reality, according to an example embodiment.

FIG. 8 illustrates an example of additional information displayed in augmented reality. As shown in FIG. 8, a camera detects a prescription pill bottle 802. In some embodiments, the camera captures the prescription pill bottle 802 and a processor performs image analysis to detect a glyph 804. In response to detecting the prescription pill bottle 802 in the field of view of the camera, the OCR module 704 can read a prescription number 806. In response to transmitting the prescription number 806 to a server (e.g. the benefit manager device 102), the user device 108 can receive additional information about the prescription drug associated with the prescription pill bottle 802, and the user device 108 can display the additional information adjacent to the prescription pill bottle 802 in augmented reality. The additional information displayed in augmented reality can include a member name 810, a photograph of a pill associated with the prescription drug 812, prescription drug information 814, a number of refills 816, refill information 818, a first interactive button 820, and a second interactive button 822. In some embodiments, the first interactive button 820 can request a refill of the prescription drug associated with the prescription pill bottle 802, and the second interactive button 822 can result in a cell phone making a call to a doctor who prescribed the prescription drug associated with the prescription pill bottle 802. However, the first and second interactive buttons 820, 822 can implement other functions. Additionally, a third interactive button can be displayed that, when activated, displays drug interaction data about the prescription drug in the prescription pill bottle 802.

Figure 9:
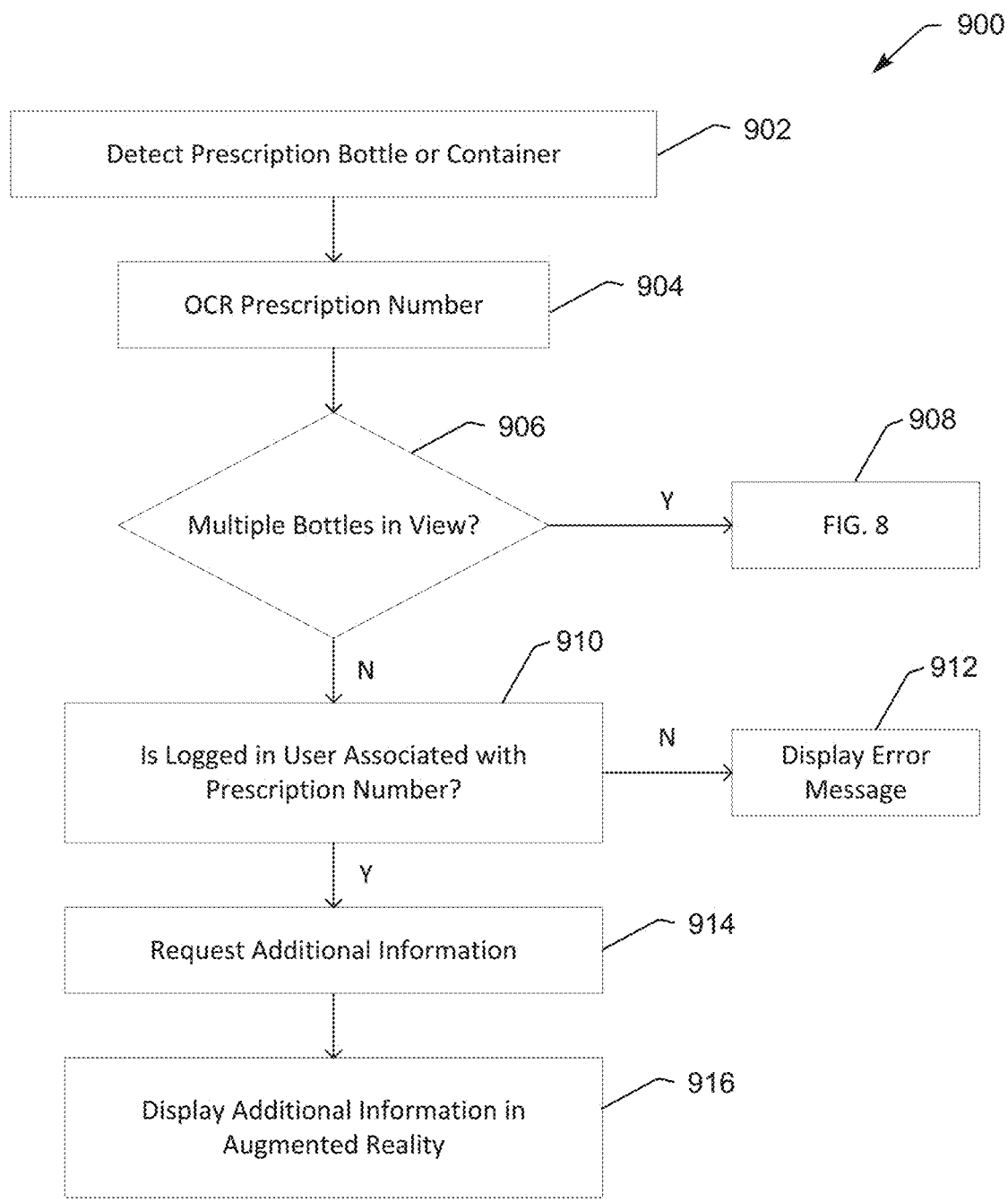
FIG. 9 is a block diagram of a flowchart illustrating methods for displaying additional information about a pharmaceutical drug in augmented reality, according to an example embodiment.

FIG. 9 illustrates a method 900 for displaying additional information about a prescription drug in augmented reality according to an example embodiment. The method 900 may be performed by the user device 108, partially by the benefit manager device 102 and partially by the user device 108, or may be otherwise performed. For the sake of simplicity, the user device 108 will be described as performing the steps of the method 900, but the embodiments described herein are not so limited.

According to an exemplary embodiment, the user device 108 can detect a prescription pill bottle or other container in step 902. According to an exemplary embodiment, the user device 108 can detect the prescription pill bottle or other container by detecting a glyph on a label of the prescription pill bottle or other container. Alternatively, the user device 108 can detect the prescription pill bottle or other container by determining that an object in the field of view of the camera matches a 3D model of the prescription pill bottle or other container.

In response to detecting the prescription pill bottle or other container in step 902, the user device 108 can search for a prescription number on the prescription pill bottle or other container and use optical character recognition (OCR) to determine the prescription number in step 904.

In step 906, the user device 108 can determine if any additional prescription pill bottles or other containers or any other substances, such as over-the-counter drugs, medical herbs, or vitamins, appear in the field of view of the camera. When multiple containers or substances appear in the field of view of the camera, the user device 108 can perform a method 1000 illustrated in FIG. 10 and described in detail below in step 908.

When only one prescription pill bottle or other container is found, the user device 108 can check to determine whether a logged-in user is associated with the prescription number in step 910. In other words, a user of the user device 108 logs into an application that performs the augmented reality functions using a member ID and password (i.e. user credentials), which can be the same as a member ID and password for a website hosted by the PBM, before performing the steps of method 900. If the logged-in user is not associated with the prescription number (e.g. the prescription is prescribed to someone else), the user device 108 can display an error message in step 912. In some embodiments, the error message can indicate that the logged-in user cannot access additional information about the drug because the drug was not prescribed to the logged-in user. The logged-in user can be associated with the prescription number by being the user (i.e. participant) to whom the prescription drug was prescribed, by being a caregiver to the participant to whom the prescription drug was prescribed, by being related to the participant to whom the prescription drug was prescribed, or by being a doctor or medical professional who prescribed the prescription drug.

If the logged-in user is associated with the prescription drug, the user device 108 can request additional information about the prescription drug by transmitting the prescription number to the benefit manager device 102 in step 914. The user device 108 can receive and display the additional information in augmented reality in step 916 (See FIG. 8)

after receiving the additional information from the benefit manager device 102. As described above, the benefit manager device 102 can receive the prescription number, use the prescription number to find additional data associated with the prescription drug (e.g. the claims data 114, and pharmaceutical drug data 118) in the database 110, and transmit the additional data to the user device 108.

Figure 10:
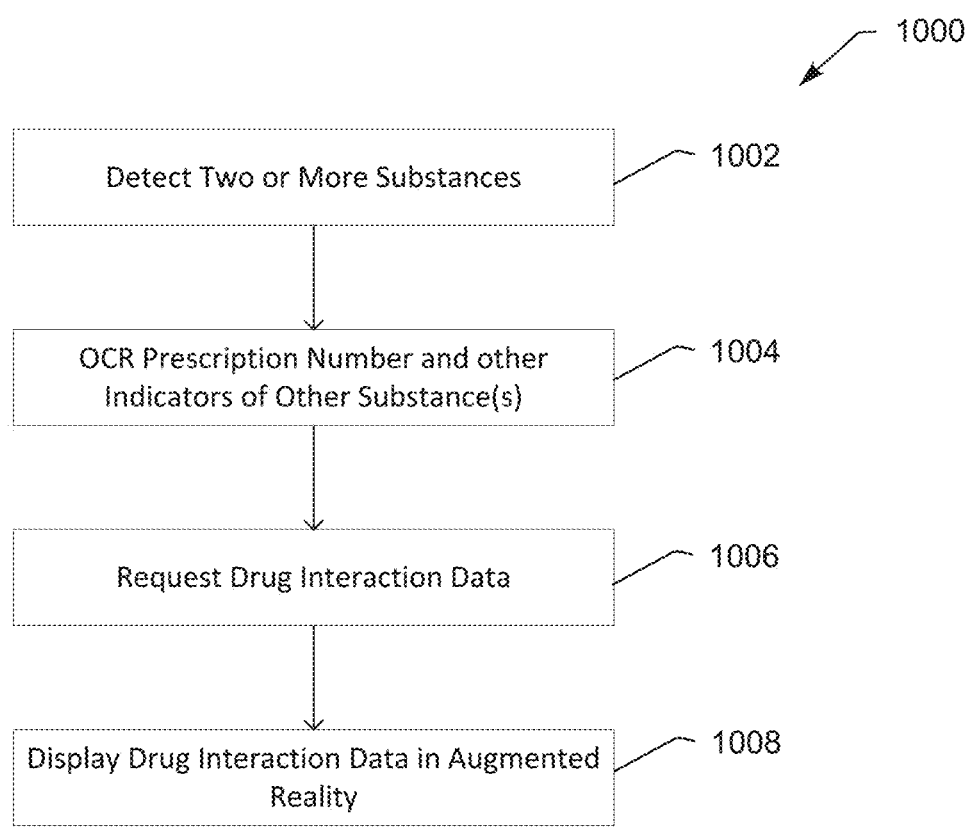
FIG. 10 is a block diagram of a flowchart illustrating methods for displaying drug interaction data in augmented reality, according to an example embodiment.

FIG. 10 illustrates a method 1000 for displaying drug interaction information about a prescription drug and another substance in augmented reality according to an example embodiment. The method 1000 may be performed by the member device 102, partially by the pharmacy benefit manager device 106 and partially by the member device 102, and/or the healthcare provider device 108, or may be otherwise performed. For the sake of simplicity, the member device 102 will be described as performing the steps of the method 1000, but the embodiments described herein are not so limited.

The member device 102 can detect multiple substances in step 1002. According to an exemplary embodiment, the member device 102 can detect prescription pill bottles or other containers by detecting multiple glyphs. Alternatively, the member device 102 can detect the multiple containers or substances by determining that multiple objects in the field of view of the camera match 3D models of the prescription pill bottles or other containers. Alternatively, the member device 102 can detect other substances by recognizing a logo or recognizing a unique pill bottle shape. In some embodiments, the member device 102 can detect substances by pill appearance or a code printed on a pill.

In response to detecting multiple prescription pill bottles or other containers in step 1002, the member device 102 can search for a prescription number and use optical character recognition (OCR) to determine the prescription number in step 1004. The member device 102 can also detect the identity of the second substance using OCR or other image recognition methods, as would be known to one having ordinary skill in the art. In some embodiments, the second substance may also have a prescription number, which is also captured using OCR.

After determining the identity of all the substances in view, the member device 102 can transmit multiple identifiers for all the substances in view to the pharmacy benefit manager device 106 in step 1006. For example, the member device 102 can transmit prescription numbers for all the substances in view, over-the-counter drug names, or any other identifiers identifying the other substances in view. The pharmacy benefit manager device 106 can use the identifiers to look up drug interaction data 120. The member device 102 can receive the drug interaction data 120 from the pharmacy benefit manager device 106 and display the drug interaction data 120 in augmented reality in step 1008.

Figure 11:
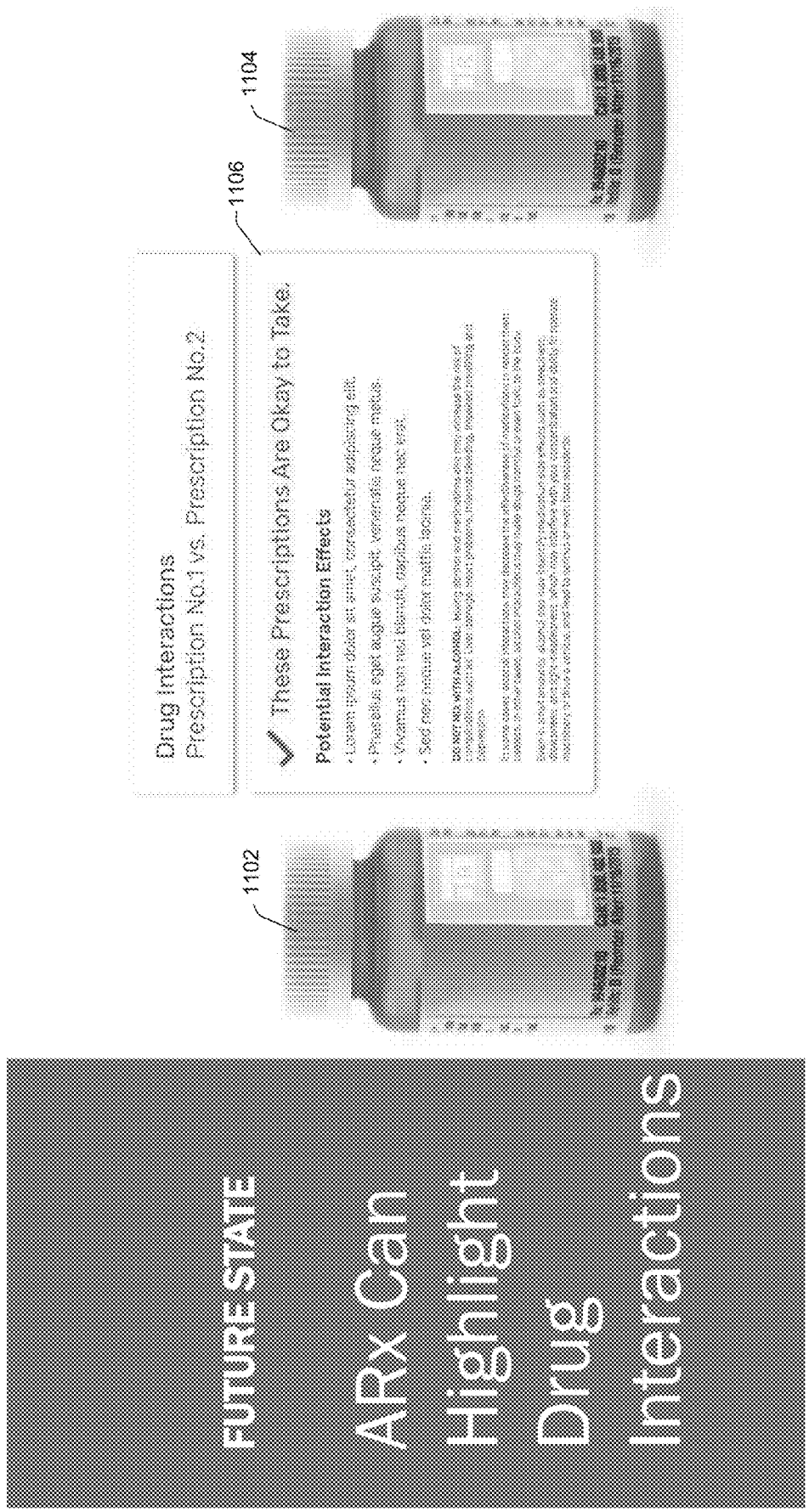
FIG. 11 is a screenshot illustrating drug interaction data displayed in augmented reality, according to an example embodiment.

FIG. 11 illustrates the member device 102 displaying the drug interaction data in augmented reality. As shown, the field of view of the camera includes a first container 1102 and a second container 1104. The member device 102 can display the drug interaction data 1106 for a substance associated with the first container 1102 and a substance associated with the second container 1104 in augmented reality. The drug interaction data 1106 can indicate that the two substances are safe to use together or the drug interaction data 1106 can display a warning altering the user not to use the two substances together. The drug interaction data 1106 can also include other warnings, such as not to use either or both substances with alcohol.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. A system comprising:
a camera;
a memory;
a display configured to receive and display a live stream of a plurality of images from within a field of view of the camera; and
a processor that (a) detects a glyph in the plurality of images by the processor performing image analysis on the plurality of images, (b) uses the glyph to identify a current location of a container within the plurality of images, wherein the glyph is contained on a sub region of the container (c) determines a first identifier associated with the container using optical character recognition, (d) determines whether a user has access to additional data about the container, (e) requests the additional data about the container from a database; and
an augmented reality subsystem configured to display the additional data about the container in an augmented reality foreground image, the augmented reality foreground image being displayed over the live stream of the plurality of images such that the additional data is displayed at a relative location adjacent to the current location and maintains the relative location as the current location changes in response to movement of the container or changes in the field of view of the camera,
wherein the additional data about the container comprises a photograph of an individual pill of a prescription drug associated with the container displayed in the augmented reality foreground image.

2. A method comprising:
receiving, from a camera, a live stream of a plurality of images from within a field of view of the camera;
performing, with a processor, image analysis on the plurality of images;
detecting, with the processor, a glyph in the plurality of images as an output of the image analysis;
an optical character recognition (OCR) processor using the glyph to identify a current location of a first prescription drug in the plurality of images;
the OCR processor determining a first identifier associated with the first prescription drug;
the OCR processor determining whether a user has access to additional data about the first prescription drug;
the OCR processor requesting the additional data about the first prescription drug from a database; and the OCR processor displaying the additional data about the first prescription drug in an augmented reality foreground image, the augmented reality foreground image being displayed over the live stream of the plurality of images such that the additional data is displayed at a relative location adjacent to the current location of the first prescription drug and maintains the relative location as the current location changes in response to movement of the first prescription drug or changes in the field of view of the camera, wherein the additional data about the container comprises a photograph of an individual pill of a prescription drug associated with the container displayed in the augmented reality foreground image.

3. The method of claim 2 wherein detecting the prescription drug in the plurality of images comprises the OCR processor detecting the glyph printed on a label on a container of the first prescription drug.

4. The method of claim 2 wherein using the glyph in the plurality of images to identify the current location of a first prescription drug in the plurality of images comprises the OCR processor determining whether an object in the plurality of images matches a 3D model of the first prescription drug.

5. The method of claim 2 wherein determining whether the user has access to the additional data about the first prescription drug comprises the OCR processor determining whether valid user credentials have been entered into an application used to display the additional data about the first prescription drug in augmented reality.

6. The method of claim 5 further comprising the OCR processor displaying an error message when the valid user credentials have not been entered into the application.

7. The method of claim 2 wherein the first identifier is a prescription number.

8. The method of claim 2 further comprising the OCR processor displaying an interactive button in augmented reality with the additional data.

9. The method of claim 8 further comprising:
the OCR processor detecting activation of the interactive button from the user; and
the OCR processor performing an action associated with the interactive button in response to the user activating the interactive button.

10. The method of claim 9 wherein the action comprises transmitting a request to refill the prescription drug to a server.

11. The method of claim 9 wherein the action comprises invoking a cellular phone function to place a phone call to a doctor who prescribed the first prescription drug.

12. The method of claim 2 wherein the additional data further comprises at least one from the group consisting of: a member name, a prescription number, a name of the first prescription drug, a quantity of the first prescription drug, a number of refills, a last fill date, a prescription expiration date, a prescribing doctor, and a prescribing doctor's phone number.

13. The method of claim 2 further comprising:
the OCR processor detecting a second substance in the plurality of images;
the OCR processor determining a second identifier associated with the second substance;
the OCR processor transmitting a request for drug interaction data between the first prescription drug and the second substance; and
the OCR processor displaying the drug interaction data in the augmented reality foreground image adjacent to the first prescription drug or the second substance.

14. The method of claim 2 further comprising:
the OCR processor predicting a number of doses remaining in a fill of the first prescription drug based on a current date, a last refill date, and dosing instructions; and
the OCR processor displaying the number of doses remaining in the fill in the augmented reality foreground image.

15. The method of claim 2 wherein determining the first identifier associated with the first prescription drug comprises the OCR processor using optical character recognition on the plurality of images.

16. The method of claim 15 further comprising the OCR processor unwarping the plurality of images before performing the optical character recognition on the image from the camera.

17. A non-transitory machine-readable medium comprising instructions, which, when executed by one or more processors, cause the one or more processors to perform the following operations:
perform image analysis on a plurality of images received in a live stream of a field of view of a camera;
detect a glyph in a plurality of images as an output of the image analysis;
use the glyph to identify a current location of a prescription drug within the plurality of images;
determine a first identifier associated with the prescription drug;
determine whether a user has access to additional data about the prescription drug;
request the additional data about the prescription drug from a database;
determine a current location of the prescription drug within the plurality of images; and
display the additional data about the prescription drug in an augmented reality foreground image, the augmented reality foreground image being displayed over the live stream of the plurality of images such that the additional data is displayed at a relative location adjacent to the current location of the prescription drug and maintains the relative location as the current location changes in response to movement of the prescription drug or changes in the field of view of the camera,
wherein the additional data about the container comprises a photograph of an individual pill of a prescription drug associated with the container displayed in the augmented reality foreground image.

* * * * *